(12) United States Patent
Nita et al.

(10) Patent No.: US 7,540,852 B2
(45) Date of Patent: Jun. 2, 2009

(54) ULTRASOUND CATHETER DEVICES AND METHODS

(75) Inventors: Henry Nita, Redwood City, CA (US); Jeff Sarge, Fremont, CA (US); Richard Spano, Gilroy, CA (US)

(73) Assignee: FlowCardia, Inc., Sunnyvale, CA (US)

( * ) Notice: Subject to any disclaimer, the term of this patent is extended or adjusted under 35 U.S.C. 154(b) by 446 days.

(21) Appl. No.: 10/927,966

(22) Filed: Aug. 26, 2004

(65) Prior Publication Data

US 2006/0047239 A1 Mar. 2, 2006

(51) Int. Cl.
*A61B 17/00* (2006.01)
(52) U.S. Cl. ........................................................ 604/22
(58) Field of Classification Search .................... 604/22, 604/113, 264; 606/169, 159, 128, 28; 600/439
See application file for complete search history.

(56) References Cited

U.S. PATENT DOCUMENTS

| | | | |
|---|---|---|---|
| 3,433,226 | A | 3/1969 | Boyd |
| 3,565,062 | A | 2/1971 | Kurls |
| 3,823,717 | A | 7/1974 | Pohlman et al. |
| 4,337,090 | A | 6/1982 | Harrison |
| 4,505,767 | A | 3/1985 | Quin |
| 4,565,589 | A | 1/1986 | Harrison |
| 4,665,906 | A | 5/1987 | Jervis |
| 4,808,153 | A | 2/1989 | Parisi |
| 4,870,953 | A | 10/1989 | DonMichael et al. |
| 4,886,060 | A | 12/1989 | Wiksell |
| 4,920,954 | A | 5/1990 | Alliger et al. |
| 4,924,863 | A | 5/1990 | Sterzer |
| 4,936,281 | A | 6/1990 | Stasz |

(Continued)

FOREIGN PATENT DOCUMENTS

DE 2438648 A1 8/1974

(Continued)

OTHER PUBLICATIONS

Calhoun et al., "Electron-beam systems for medical device sterilization" downloaded from web on Oct. 8, 2002 <http://www.devicelink.com/mpb/archive/97/07/002.html> 7 pages total.

(Continued)

*Primary Examiner*—Nicholas D Lucchesi
*Assistant Examiner*—Christopher D Koharski
(74) *Attorney, Agent, or Firm*—Townsend and Townsend and Crew LLP

(57) ABSTRACT

Ultrasound catheter devices and methods provide enhanced disruption of blood vessel obstructions. Generally, an ultrasound catheter device includes an elongate flexible catheter body with one or more lumens, an ultrasound transmission member extending longitudinally through the catheter body lumen and a distal head coupled with the transmission member and positioned adjacent the distal end of the catheter body for disrupting occlusions. A proximal housing of the catheter device may include one or more features for dissipating heat from the ultrasound transmission wire, such as a fluid inlet aperture for passage of fluid, use of heat conductive materials in the proximal housing, surface features to increase the housing's surface area, heat conductive members disposed adjacent the transmission member and the like. Various irrigation fluids may be used, such as cooled, oxygen supersaturated or lubricious fluids.

37 Claims, 5 Drawing Sheets

U.S. PATENT DOCUMENTS

| | | | |
|---|---|---|---|
| 5,000,185 A | | 3/1991 | Yock |
| 5,248,296 A | | 9/1993 | Alliger |
| 5,267,954 A | | 12/1993 | Nita |
| 5,312,328 A | | 5/1994 | Nita et al. |
| 5,324,260 A | * | 6/1994 | O'Neill et al. ......... 604/103.08 |
| 5,325,860 A | | 7/1994 | Seward et al. |
| 5,342,292 A | * | 8/1994 | Nita et al. ..................... 604/22 |
| 5,368,558 A | * | 11/1994 | Nita ............................. 604/22 |
| 5,380,274 A | | 1/1995 | Nita |
| 5,382,228 A | | 1/1995 | Nita et al. |
| 5,397,293 A | | 3/1995 | Alliger et al. |
| 5,397,301 A | | 3/1995 | Pflueger et al. |
| 5,417,672 A | | 5/1995 | Nita et al. |
| 5,540,656 A | | 7/1996 | Pflueger et al. |
| 5,542,917 A | | 8/1996 | Nita et al. |
| 5,597,882 A | | 1/1997 | Schiller et al. |
| 5,916,192 A | | 6/1999 | Nita et al. |
| 5,916,912 A | | 6/1999 | Ames et al. |
| 5,957,882 A | * | 9/1999 | Nita et al. ..................... 604/22 |
| 5,967,984 A | | 10/1999 | Chu et al. |
| 5,989,208 A | | 11/1999 | Nita |
| 5,997,497 A | | 12/1999 | Nita et al. |
| 6,007,499 A | | 12/1999 | Martin et al. |
| 6,007,514 A | * | 12/1999 | Nita ............................. 604/22 |
| 6,165,127 A | | 12/2000 | Crowley |
| 6,217,543 B1 | * | 4/2001 | Anis et al. ..................... 604/22 |
| 6,241,692 B1 | | 6/2001 | Tu et al. |
| 6,296,620 B1 | | 10/2001 | Gesswein et al. |
| 6,315,741 B1 | | 11/2001 | Martin et al. |
| 6,379,378 B1 | * | 4/2002 | Werneth et al. ............ 607/105 |
| 6,394,956 B1 | | 5/2002 | Chandrasekaran et al. |
| 6,398,736 B1 | | 6/2002 | Seward |
| 6,416,533 B1 | * | 7/2002 | Gobin et al. ................ 607/113 |
| 6,454,757 B1 | | 9/2002 | Nita et al. |
| 6,508,781 B1 | * | 1/2003 | Brennan et al. ............... 604/22 |
| 6,573,470 B1 | * | 6/2003 | Brown et al. ............. 219/86.51 |
| 6,685,657 B2 | | 2/2004 | Jones |
| 6,936,056 B2 | | 8/2005 | Nash et al. |
| 6,942,677 B2 | * | 9/2005 | Nita et al. ................... 606/169 |
| 2003/0216732 A1 | * | 11/2003 | Truckai et al. ................ 606/49 |
| 2004/0167507 A1 | * | 8/2004 | Nita et al. ..................... 606/27 |

FOREIGN PATENT DOCUMENTS

| | | |
|---|---|---|
| DE | 3821836 A1 | 6/1988 |
| EP | 316789 B1 | 11/1988 |
| WO | WO 87/05739 A1 | 9/1987 |
| WO | WO 89/06515 A1 | 7/1989 |
| WO | WO 90/01300 A1 | 2/1990 |

OTHER PUBLICATIONS

E-Beam Theory RDI-IBA Technology Group, downloaded from web on Oct. 8, 2002 <http://www.e-beam-rdi/EbeamTheory.htm> 2 pages total.

Health Care Without Harm [report], "Irradiation, biological, and other technologies: E-beam, biological, and sharps treatment systems", Chapter 9, *Non-Incineration Medical Waste Treatment Technologies*, Aug. 2001, pp. 69-74.

What is electron beam curing? downloaded from web on Nov. 14, 2002 <http://www.ms.ornl.gov/researchgroups/composites/new%20orccmt%20pages/pages/ebwha> 4 pages total.

* cited by examiner

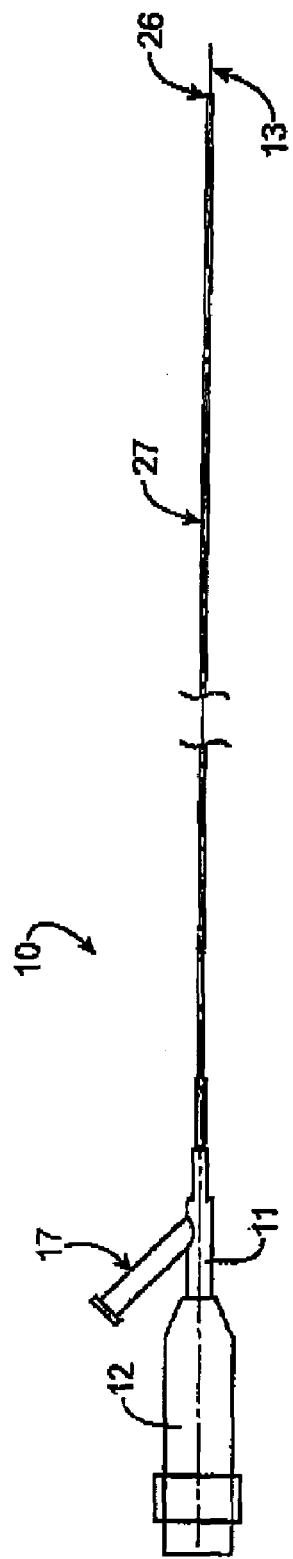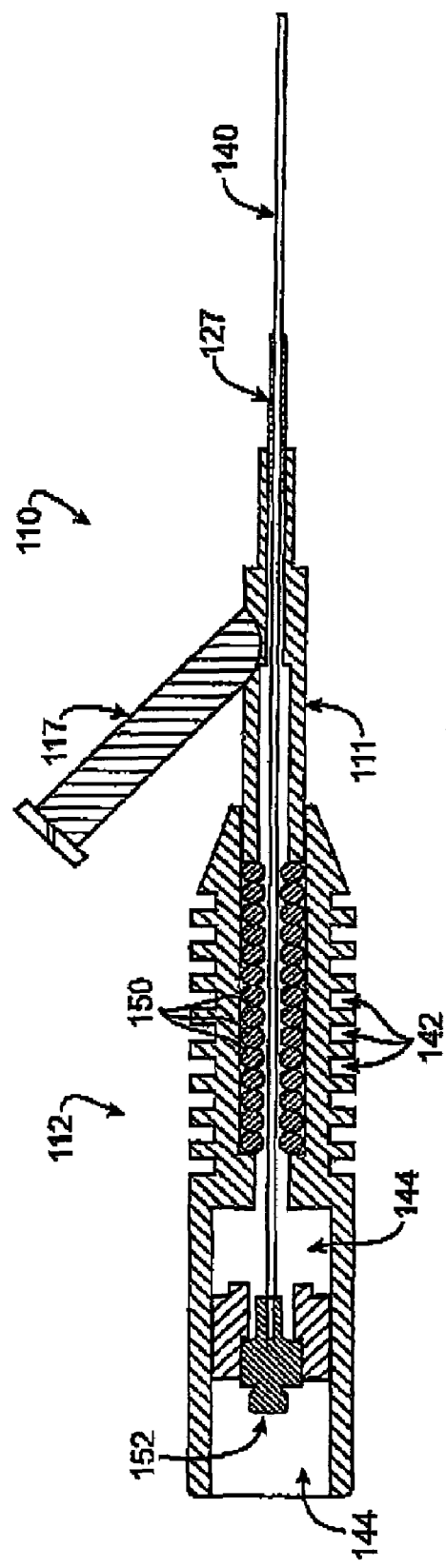
FIG. 2
FIG. 3

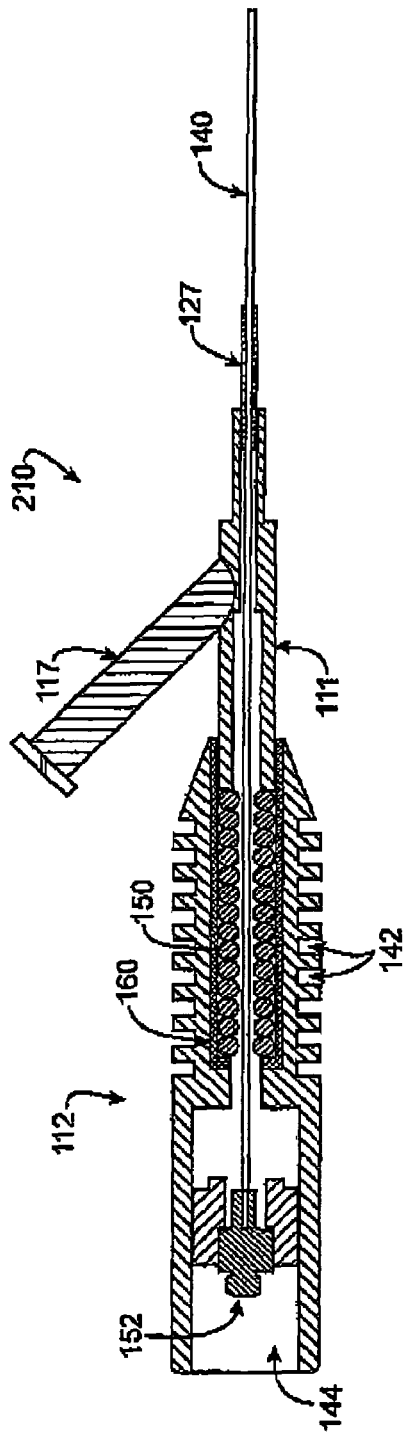
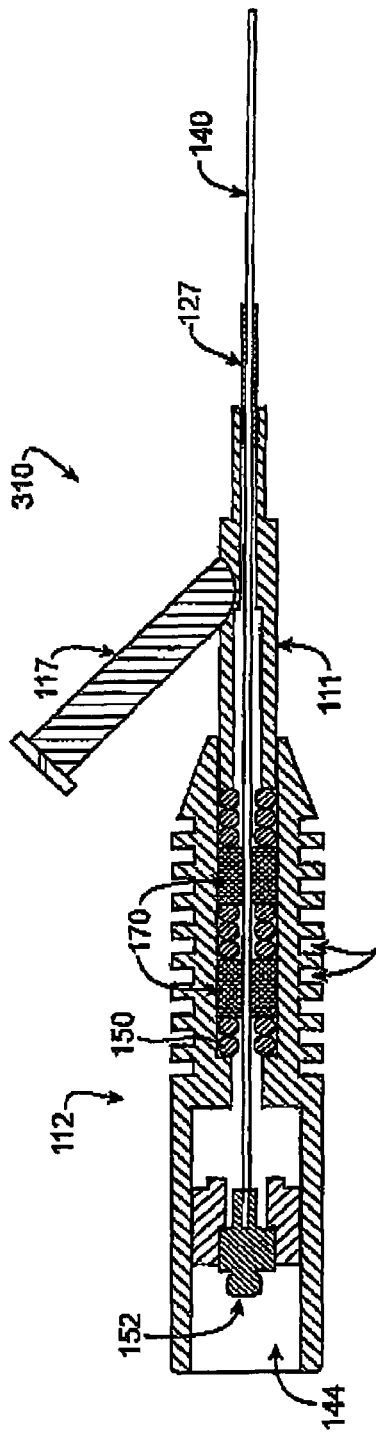
FIG. 4
FIG. 5

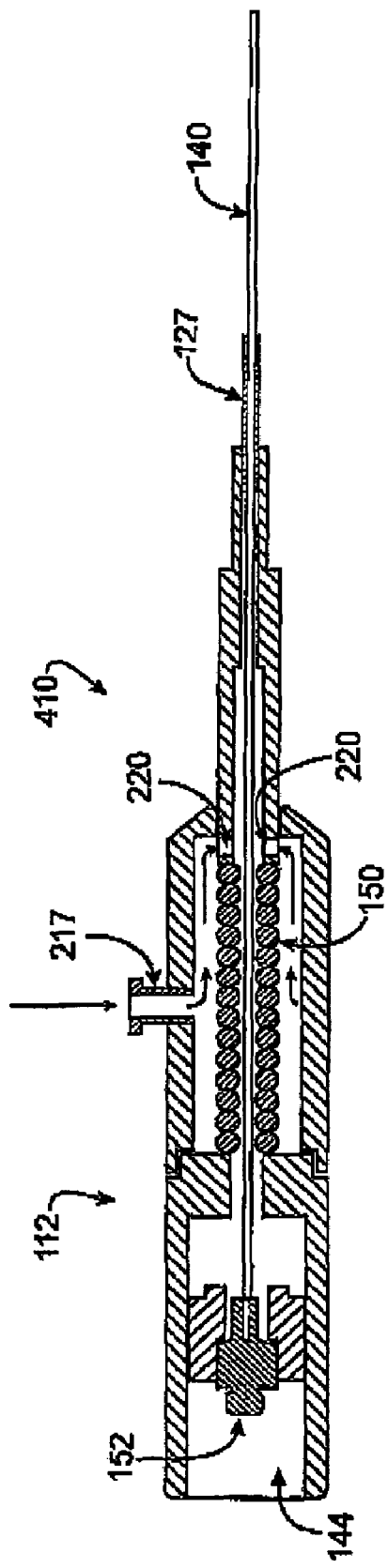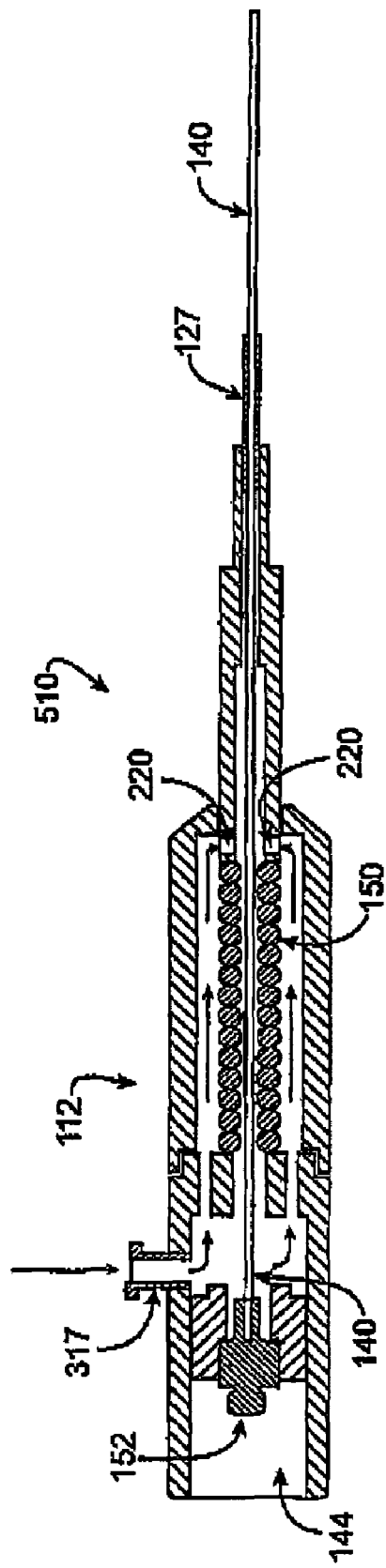

ULTRASOUND CATHETER DEVICES AND METHODS

This application is related to the following U.S. Patent Application Serial Nos.: Ser. No. 10/229,371, filed Aug. 26, 2002, entitled "Ultrasound Catheter for Disrupting Blood Vessel Obstructions"; Ser. No. 10/345,078, filed Jan. 14, 2003, entitled "Ultrasound Catheter and Methods for Making and Using Same"; Ser. No. 10/375,903, filed Feb. 26, 2003, entitled "Ultrasound Catheter Apparatus"; Ser. No. 10/410,617, filed Apr. 8, 2003, entitled "Improved Ultrasound Catheter Devices and Methods"; and Ser. No. 10/722,209, filed Nov. 24, 2003, entitled "Steerable Ultrasound Catheter". The full disclosures of all of the above-listed patent applications are all hereby incorporated by reference.

BACKGROUND OF THE INVENTION

The present invention relates generally to medical devices and methods. More specifically, the present invention relates to ultrasound catheter devices and methods for treating occlusive intravascular lesions.

Catheters employing various types of ultrasound transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various ultrasonic catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), U.S. Pat. No. 4,936,281 (Stasz), U.S. Pat. No. 3,565,062 (Kuris), U.S. Pat. No. 4,924,863 (Sterzer), U.S. Pat. No. 4,870,953 (Don Michael, et al), and U.S. Pat. No. 4,920,954 (Alliger, et al.), as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2438648 (Pohlman). While many ultrasound catheters have been developed, however, improvements are still being pursued.

Typically, an ultrasonic catheter system for ablating occlusive material includes three basic components: an ultrasound generator, an ultrasound transducer, and an ultrasound catheter. The generator converts line power into a high frequency current that is delivered to the transducer. The transducer contains piezoelectric crystals which, when excited by the high frequency current, expand and contract at high frequency. These small, high-frequency expansions (relative to an axis of the transducer and the catheter) are amplified by the transducer horn into vibrational energy. The vibrations are then transmitted from the transducer through the ultrasound catheter via an ultrasound transmission member (or wire) running longitudinally through the catheter. The transmission member transmits the vibrational energy to the distal end of the catheter where the energy is used to ablate or otherwise disrupt a vascular obstruction.

To effectively reach various sites for treatment of intravascular occlusions, ultrasound catheters of the type described above typically have lengths of about 150 cm or longer. To permit the advancement of such ultrasound catheters through small and/or tortuous blood vessels such as the aortic arch, coronary vessels, and peripheral vasculature of the lower extremities, the catheters (and their respective ultrasound transmission wires) must typically be sufficiently small and flexible. Also, due to attenuation of ultrasound energy along the long, thin, ultrasound transmission wire, a sufficient amount of vibrational energy must be applied at the proximal end of the wire to provide a desired amount of energy at the distal end.

One continuing challenge in developing ultrasound catheters for treating vascular occlusions is to provide adequate vibrational energy at the distal end of a catheter device without overheating the ultrasound transmission wire. Generally, increasing the amount of power input to the ultrasound transmission wire causes the temperature of the wire to increase. Overheating may occur anywhere along the length of the transmission wire, from its proximal connection with the ultrasound transducer to the distal tip of the wire. Overheating of the wire, along with the mechanical stresses placed on the wire from propagating ultrasound waves, can cause wire breakage, thus shortening the useful life of the catheter device. Furthermore, it is generally desirable to ablate an occlusion via the ultrasound vibrations and not by heating the occlusion, since heating causes a denaturalization process that reduces the efficacy of the ultrasound ablation.

Some ultrasound catheters use irrigation fluid to attempt to control the temperature of the ultrasound transmission wire, but such irrigation cooling techniques are not always effective. Other devices use swapped frequencies to change frequency nodes and anti-nodes, thus moving a heat source from point to point along the transmission wire. However, a given ultrasound transmission wire resonates at the fundamental frequency for which it is designed, and thus changing frequencies essentially requires turning the ultrasound device on and off, which reduces the efficacy of the device. Some ultrasound catheter devices include one or more absorption members at the proximal end for absorbing unwanted vibrations of the ultrasound transmission wire. Such absorbers, however, do not address the heat generation issue and, in fact, may cause increased heating from frictional forces.

Therefore, a need exists for improved ultrasound catheter devices and methods that provide ablation or disruption of vascular occlusions. Ideally, such ultrasound catheters would provide a desired level of power at a distal end of the device while also preventing overheating of the device's ultrasound transmission member. Ideally, such devices would address ultrasound transmission wire overheating at its proximal connection with a catheter device as well as along the length of the wire. At least some of these objectives will be met by the present invention.

BRIEF SUMMARY OF THE INVENTION

In one aspect of the invention, an ultrasound catheter for disrupting occlusions in blood vessels includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a proximal housing coupled with the proximal end of the catheter body and housing the sonic connector and a proximal portion of the ultrasound transmission wire. The proximal housing includes at least one heat dissipation feature for dissipating heat from the proximal portion of the ultrasound transmission member.

In some embodiments, the heat dissipation feature comprises one or more portions of the housing constructed of a heat conductive material. For example, the heat conductive material may include, but is not limited to, metal, polymer, glass, rubber, combinations thereof, or the like. Additionally (or alternatively), the heat dissipation feature may comprise multiple surface features on the housing to increase a surface area of the housing. Such surface features may include, for example, grooves, notches, waves, dips and/or the like. In some embodiments, an additional or alternative heat dissipation feature comprises at least one conductive material disposed within the housing, at least partially encircling the ultrasound transmission member, to conduct heat away from the ultrasound transmission member. In one embodiment, the conductive material may be disposed adjacent one or more vibration absorption members surrounding the ultrasound transmission member. Optionally, multiple separate conductive members may be disposed between multiple vibration absorption members to at least partially encircle the ultrasound transmission member. In another embodiment, the conductive material is arranged over one or more vibration absorption members surrounding the ultrasound transmission member.

In some embodiments, the heat dissipation feature comprises at least one fluid inlet for allowing passage of one or more heat dissipating fluids into an inner cavity of the housing. In some embodiments, the inner cavity of the housing is in fluid communication with the lumen of the catheter body, such that fluid introduced into the inner cavity passes through and out a distal end of the catheter body lumen. In some embodiments, the inlet is disposed along the housing such that the heat dissipating fluid(s) passing through the inlet contact at least one vibration absorption member disposed over the ultrasound transmission member. The inlet may also be disposed along the housing such that the heat dissipating fluid(s) passing through the inlet contact the sonic connector and a portion of the ultrasound transmission member. Some devices further include a refrigeration device coupled with the catheter for refrigerating a fluid to be introduced through the fluid inlet. Optionally, the device may further include a guidewire tube extending through at least a portion of the catheter body for allowing passage of a guidewire. In one embodiment, a sidewall of the guidewire tube includes a plurality of apertures for allowing fluid introduced into the lumen of the catheter body to pass into and through the guidewire tube.

In some embodiments, at least a portion of the proximal housing comprises a material adapted to change color when the temperature of the housing changes. In one embodiment, for example, the material comprises a thermochromic pigment. The thermochromic pigment, in one embodiment, may change from a first color to a second color when the temperature of the housing reaches approximately 45° Celsius and changes from the second color to the first color when the temperature of the housing drops below approximately 45° Celsius.

In another aspect of the present invention, an ultrasound catheter for disrupting occlusions in blood vessels includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; a proximal housing coupled with the proximal end of the catheter body and housing the sonic connector and a proximal portion of the ultrasound transmission wire; and heat dissipation means for dissipating heat from the ultrasound transmission member. According to various embodiments, heat dissipation means may include any suitable members, devices, attachments or the likes, such as but not limited to those described above. Any features described above may be applied to this ultrasound catheter.

In another aspect of the present invention, an ultrasound catheter system for disrupting occlusions in blood vessels includes an ultrasound catheter device, an ultrasound generator removably coupled with the ultrasound catheter device, and a fluid cooling device removably coupled with the ultrasound catheter device for cooling one or more heat dissipating fluids to be passed through the catheter device. The ultrasound catheter device itself includes: an elongate flexible catheter body having a proximal end, a distal end and at least one lumen; an ultrasound transmission member extending longitudinally through the lumen of the catheter body and having a proximal end and a distal end; a distal head coupled with the distal end of the ultrasound transmission member and disposed adjacent the distal end of the catheter body; a sonic connector coupled with the proximal end of the ultrasound transmission member for coupling the ultrasound transmission member with an ultrasound transducer device; and a proximal housing coupled with the proximal end of the catheter body and housing the sonic connector and a proximal portion of the ultrasound transmission wire. The housing includes at least one fluid inlet for allowing passage of one or more heat dissipating fluids into an inner cavity of the housing. Again, the ultrasound catheter may include any of the features described above.

In another aspect of the present invention, a method for disrupting an occlusion in a blood vessel involves positioning an ultrasound catheter in the blood vessel such that a distal end of the catheter is adjacent the occlusion; transmitting ultrasound energy to an ultrasound transmission member of the ultrasound catheter to disrupt the occlusion into multiple occlusion fragments, and passing a cooled irrigation fluid through the ultrasound catheter to dissipate heat away from the ultrasound transmission member. In some embodiments, for example, the cooled fluid has a temperature between about 1° C. and about 22° C. Any suitable cooled fluid may be used, such as but not limited to saline, thrombolytic agents, antiplatelet drugs, lysing agents, anticoagulants and/or the like. In some embodiments, the method further involves cooling the irrigation fluid to a desired temperature, using a refrigeration device coupled with the ultrasound catheter. In one embodiment, cooled fluid is passed continuously through the ultrasound catheter during an occlusion disruption procedure. Alternatively, the cooled fluid may be passed through the ultrasound catheter while the catheter is activated, with fluid passage being automatically stopped when the ultrasound catheter is deactivated.

In another aspect of the present invention, a method for disrupting an occlusion in a blood vessel involves positioning an ultrasound catheter in the blood vessel such that a distal end of the catheter is adjacent the occlusion, transmitting ultrasound energy to an ultrasound transmission member of the ultrasound catheter to disrupt the occlusion into multiple occlusion fragments, and passing an oxygen supersaturated irrigation fluid through the ultrasound catheter to dissipate heat away from the ultrasound transmission member. In some embodiments, for example, the oxygen supersaturated irrigation fluid comprises oxygen supersaturated saline solution. In other embodiments, the oxygen supersaturated irrigation fluid comprises saline solution combined with a radiopaque contrast material. The oxygen supersaturead fluid may be kept at any suitable temperature. In some embodiments, the fluid is kept at room temperature, while in other embodiments it is kept at between about 1° C. and about 22° C.

In another aspect of the present invention, a method for disrupting an occlusion in a blood vessel involves positioning an ultrasound catheter in the blood vessel such that a distal end of the catheter is adjacent the occlusion, transmitting ultrasound energy to an ultrasound transmission member of the ultrasound catheter to disrupt the occlusion into multiple occlusion fragments, and passing a lubricious irrigation fluid through the ultrasound catheter to dissipate heat away from the ultrasound transmission member and reduce friction between the ultrasound transmission member and an ultrasound catheter body. For example, in some embodiments, the lubricious irrigation fluid comprises an emulsion. In one embodiment, the emulsion comprises olive oil, egg yolk, phospholipids, glycerin, sodium deoxycholate, L-histidine, disodium CDTA, sodium hydroxide and water. In some embodiments, the emulsion has a pH of between about 8.0 and about 9.0. The lubricious fluid may be kept at any suitable temperature. In some embodiments, the fluid is kept at room temperature, while in other embodiments it is kept at between about 1° C. and about 22° C.

These and other aspects and embodiments of the present invention are described in further detail below, in reference to the attached drawing figures.

BRIEF DESCRIPTION OF THE DRAWINGS

FIG. 2 is a side view of an ultrasound catheter device according to an embodiment of the present invention;

FIG. 3 is cross-sectional side view of a proximal portion of an ultrasound catheter device having heat dissipation means according to an embodiment of the present invention;

FIG. 4 is cross-sectional side view of a proximal portion of an ultrasound catheter device having heat dissipation means according to another embodiment of the present invention;

FIG. 5 is cross-sectional side view of a proximal portion of an ultrasound catheter device having heat dissipation means according to another embodiment of the present invention;

FIG. 6 is cross-sectional side view of a proximal portion of an ultrasound catheter device, with a proximal housing of the device having a fluid inlet aperture according to an embodiment of the present invention;

FIG. 7 is cross-sectional side view of a proximal portion of an ultrasound catheter device, with a proximal housing of the device having a fluid inlet aperture according to another embodiment of the present invention.

DETAILED DESCRIPTION OF THE INVENTION

Ultrasound catheter devices and methods of the present invention provide for disruption of occlusions in blood vessels. Catheter devices generally include a catheter body, an ultrasound energy transmission member disposed within the catheter body and a distal head coupled with the energy transmission member and disposed at or near the distal end of the catheter body. The ultrasound transmission member transmits ultrasound energy from an ultrasound transducer to the distal head, causing the head to vibrate and, thus, disrupt vascular occlusions. A number of improved features of such ultrasound catheter devices are described more fully below.

Figure 1:
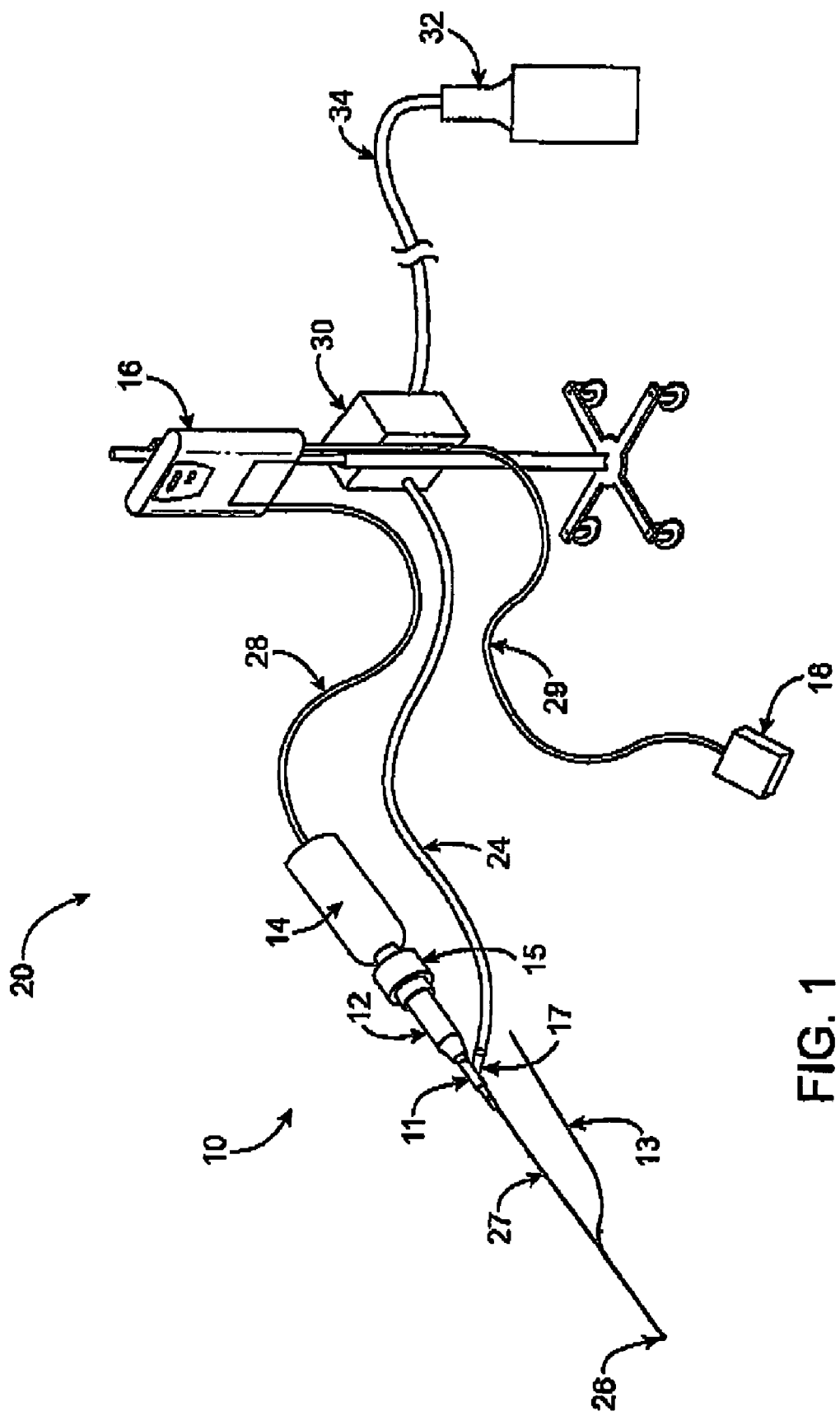
FIG. 1 is a perspective view of an ultrasound catheter system according to an embodiment of the present invention.

Referring now to FIG. 1, one embodiment of an ultrasound catheter system 20 suitably includes an ultrasound catheter device 10 and an ultrasound generator 16. Catheter device 10 suitably includes a distal head 26 for disrupting occlusions, a catheter body 27, and a proximal end connector 12 for coupling catheter device 10 with an ultrasound transducer 14. Ultrasound transducer 14 is coupled with ultrasound generator 16 via a connector 28, and generator is coupled with a foot-actuated on/off switch 18 via another connector 29. Generator 16 provides ultrasonic energy to transducer 14 and, thus, to ultrasound catheter 10. Catheter device 10 further includes an ultrasound transmission member (or "wire"—not shown) that extends through the catheter body 27 and transmits energy from the transducer 14 to the distal head 26. Some embodiments of device 10 include a rapid exchange guidewire 13 and guidewire port, while other embodiments include a proximal guidewire port for over the wire guidewire delivery. In some embodiments, transducer 14 further includes a securing device 15 for enhancing coupling of catheter 10 to transducer 14. The various components of system 20 may be coupled via any suitable means. Connectors 28, 29 may comprise an electric cord or cable or any other suitable connecting devices for coupling on/off switch 18, generator 16 and transducer 14. In an alternative embodiment, on/off swith 18 is located on generator 16.

In addition to proximal connector 12, ultrasound catheter device 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigeration (or "fluid cooling") device 30. Refrigeration device 30 may, in turn, be coupled with a fluid container 32 via a connector tube 34. This irrigation apparatus may be used for introducing one or more fluids into catheter device 10. Fluid may be used to cool any part of the device, such as the ultrasound transmission member, thus helping reduce wear and tear of device 10. In some embodiments, fluid inlet port 17 is located farther proximally on proximal connector 12, to allow fluid to be applied within connector 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigeration device 30 and fluid container 32 are combined in one device.

Generally, catheter device 10 may include any suitable number of side-arms or ports for passage of a guidewire, application of suction, infusing and/or withdrawing irrigation fluid, dye and/or the like, or any other suitable ports or connections. Also, ultrasound catheters 10 of the present invention may be used with any suitable proximal devices, such as any suitable ultrasound transducer 14, ultrasound generator 16, coupling device(s) and/or the like. Therefore, the exemplary embodiment shown in FIG. 1 and any following descriptions of proximal apparatus or systems for use with ultrasound catheters 10 should not be interpreted to limit the scope of the present invention as defined in the appended claims.

Referring now to FIG. 2, an enlarged view of catheter device 10 is shown. Proximal connector 12, Y-connector 11, inlet port 17, catheter body 27, distal head 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some ultrasound catheters have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

Features of the present invention may be applied to any of a number of ultrasound catheter devices. For more detailed description of exemplary ultrasound catheter devices, reference may be made to U.S. patent application Ser. Nos. 10/229,371, 10/345,078, 10/375,903, 10/410,617 and 10/722,209, which were all previously incorporated by reference. In various alternative embodiments, aspects of the present invention may be applied to any other suitable catheter devices.

Referring now to FIG. 3, a proximal portion of one embodiment of an ultrasound catheter device 110 is shown in cross-section. An ultrasound transmission wire 140 extends from a sonic connector 152 distally to a distal end (not shown) of catheter device 110. A catheter body 127 of device 110 is shown only in part, whereas catheter body 127 typically extends distally to (or near) the distal end of device 110. Catheter device 110 also includes a proximal housing 112 (or "proximal connector"), having an inner bore 144 (or "inner cavity") in which sonic connector 152, a portion of ultrasound transmission member 140 and one or more vibration absorption members 150 reside. Housing 112 is coupled with a Y-connector 111, which includes a fluid inlet port 117 (or aperture), and Y-connector 111 is coupled with catheter body 127.

In various embodiments, housing 112 may suitably include one or more surface features 142 for increasing the overall surface area of the outer surface of housing 112. Increased surface area enhances the ability of housing 112 to dissipate heat generated by ultrasound transmission member 140 out of catheter device 110. Surface features 142 may have any suitable size or shape, such as ridges, jags, undulations, grooves or the like, and any suitable number of surface features 142 may be used. Additionally, housing 112 may be made of one or more heat dissipating materials, such as aluminum, stainless steel, any other conductive metal(s), or any suitable nonmetallic conductive material(s).

In most embodiments, ultrasound transmission member 140, wire, or wave guide extends longitudinally through a lumen of catheter body 127 to transmit ultrasonic energy from an ultrasound transducer (not shown), connected to the proximal end of proximal housing 112, to the distal end of catheter device 110. Ultrasound transmission member 140 may be formed of any material capable of effectively transmitting ultrasonic energy from the ultrasound transducer to the distal end of catheter body 127, including but not limited to metals such as pure titanium or aluminum, or titanium or aluminum alloys. Again, additional details of ultrasound transmission members 140 may be found in the patent applications incorporated by reference above. Similarly, reference may be made to the incorporated patent applications for descriptions of housing 112, sonic connector 152, vibration absorption members 150, Y-connector 111 and the like. For example, housing 112 and other features are described in detail in Ser. No. 10/722,209, filed Nov. 24, 2003, entitled "Steerable Ultrasound Catheter", which was previously incorporated by reference.

Ultrasound transmission member 140 typically passes from sonic connector 152, through bore 144 and Y-connector 111, and then through catheter body 127. Fluid inlet port 117 is in fluid communication with a lumen in Y-connector, which is in fluid communication with a lumen extending through catheter body 127. Thus, fluid introduced into fluid inlet port 117 is typically free to flow into and through catheter body 127 to contact ultrasound transmission member 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, super-saturated saline or contrast/saline mixture, or the like. Cooling and/or lubricating ultrasound transmission member 140 may reduce friction and/or wear and tear of ultrasound transmission member 140, thus prolonging the useful life of ultrasound catheter device 110 and enhancing its performance.

Additionally, the temperature and flow rate of a coolant liquid may be specifically controlled to maintain the temperature of ultrasound transmission member 140 at a desired temperature within its optimal working range. In particular, in embodiments of the invention where ultrasound transmission member 140 is formed of a metal alloy which exhibits optimal physical properties (e.g. super elasticity) within a specific range of temperatures, the temperature and flow rate of coolant liquid infused through fluid inlet port 117 may be specifically controlled to maintain the temperature of ultrasound transmission member 140 within a range of temperatures at which it demonstrates its most desirable physical properties. For example, in embodiments of the invention where ultrasound transmission member 140 is formed of a shape memory alloy which exhibits super-elasticity when in its martensite state, but which loses super-elasticity as it transitions to an austenite state, it will be desirable to adjust the temperature and flow rate of the coolant liquid infused through fluid inlet port 117 to maintain the shape memory alloy of ultrasound transmission member 140 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through port 117 will be at such temperature, and will be infused at such rate, as to maintain the shape memory alloy of ultrasound transmission member 140 below its martensite transition temperature.

As mentioned above, in one embodiment, a super-saturated fluid may be used. Use of such fluids may enhance cavitation of an occlusion, help prevent unwanted tissue damage and/or the like. Such fluids are described, for example, in U.S. Pat. Nos. 6,676,900, 6,622,542, 6,613,280, 6,607,698, 6,605,217, 6,602,468, 6,602,467, 6,596,235, 6,582,387, 6,576,807, 6,558,502, 6,555,059, 6,533,766, 6,454,997, 6,387,324, 6,346,192, 6,315,754, 6,248,087, 6,235,007, 6,180,059, 6,142,971, 6,123,698, 6,030,357, 5,976,119, 5,957,889, 5,893,838 and 5,797,876, which are hereby incorporated by reference. In another embodiment, a mixture of contrast dye and saline may be used to achieve the same or similar results.

With reference now to FIG. 4, one embodiment of an ultrasound catheter device 210 includes the features described immediately above and also includes a heat absorbing member 160 disposed within housing 112. Heat absorbing member 160 may have any suitable shape and size and may, in various embodiments, be disposed in any of a number of different locations within housing 112. Typically, heat absorbing member 160 is made of a heat absorbing material, such as but not limited to a metalized elastomer, such as a rubber material combined with a metallic powder such as aluminum powder. Of course, any other suitable heat sink or heat absorption material may be used, in alternative embodiments. In the embodiment shown, heat absorbing member 160 is generally cylindrical in shape and is disposed around vibration absorption members 150, so that it absorbs heat from ultrasound transmission member 140 and vibration absorbers 150.

Referring to FIG. 5, in an alternative embodiment an ultrasound catheter device 310 may include multiple heat absorption members 170, such as cylindrical members disposed around ultrasound transmission member 140 and in between multiple vibration absorption members 150. As is evident from FIGS. 4 and 5, any of a number of configurations of heat absorption members 160, 170 may be disposed within housing 112.

FIG. 6 demonstrates another embodiment of an ultrasound catheter device 410, which may include any of the features described above. In this embodiment, a fluid inlet port 217 is located farther proximally on housing 112 than in the earlier-described embodiments. Fluid inlet port 217 is in fluid communication with inner cavity 144 of housing 112, so that fluid (solid-tipped arrows) introduced into fluid inlet port 217 enters inner cavity 144 and contacts vibration absorption members 150 before entering the lumen of catheter body 127 via one or more proximal apertures 220. Fluid passing along and contacting vibration absorption members 150 will help dissipate heat from the members 150. As mentioned above, such fluids may be refrigerated/cooled, lubricious, oxygen supersaturated or the like. Lubricious and oxygen supersaturated fluids, in various embodiments, may be either cooled/refrigerated or at room temperature.

Referring to FIG. 7, another embodiment of an ultrasound catheter device 510 includes all the features just described, but fluid inlet port 317 is located farther proximally on housing 112. In this embodiment, fluid (solid-tipped arrows) entering fluid inlet port 317 contacts a proximal portion of ultrasound transmission member 140, proceeds distally to contact vibration absorption members 150, and then proceeds through apertures 220 into the lumen of catheter body 127. Thus, the fluid provides extra heat dissipation to the proximal portion of ultrasound transmission member 140 with which it comes in contact.

Figure 8:
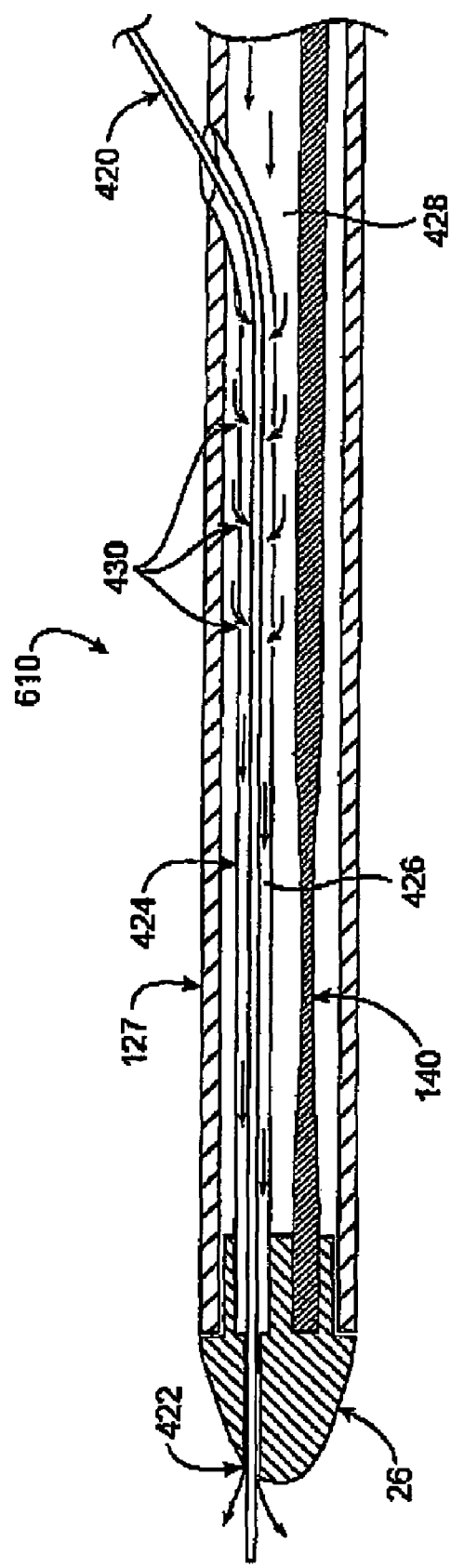
FIG. 8 is a cross-sectional side view of a distal portion of an ultrasound catheter device having a perforated guidewire tube for allowing passage of fluid therethrough according to another embodiment of the present invention

As mentioned above, in some embodiments irrigation/cooling fluid passes through a lumen of catheter body 127 and out one or more apertures in distal head 26 or elsewhere on the catheter device. In an alternative embodiment, and with reference now to FIG. 8, an ultrasound catheter device 610 may include a guidewire tube 424 that forms a guidewire lumen 426 and that includes one or more guidewire tube apertures 430 for allowing passage of fluid. Generally, a guidewire 420 may be passed through guidewire lumen 426 and out a distal aperture 422 of guidewire tube 424, located in distal head 26. Fluid (solid-tipped arrows) that is passed through a catheter body lumen 428 may flow into apertures 430 and out distal aperture 422. The fluid would thus contact ultrasound transmission member 140 during a portion of its journey through catheter body lumen 428, thus dissipating heat and/or lubricating, and would then pass out of catheter device 610 via guidewire tube 424. This configuration may be advantageous in that irrigation fluid may provide an additional lubrication inside guidewire lumen 426 to improve guidewire movement.

In one embodiment, housing 112 may include a material that changes color when its temperature increases or decreases, thus providing an indication of the temperature of the proximal portion of the catheter device. In one embodiment, for example, a thermochromic material, such as Colorcomp® Thermochromics (provided by LNP Engineering Plastics, Inc.) may be used. Other color-change materials may be used in alternative embodiments. In various embodiments, the color of such material may change at any suitable temperatures. In one embodiment, for example, the thermochromic pigment changes from a first color to a second color when the temperature of housing 112 reaches approximately 45° Celsius and changes from the second color to the first color when the temperature of housing 112 drops below approximately 45° Celsius.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. An ultrasound catheter for disrupting occlusions in blood vessels, the ultrasound catheter comprising:
   an elongate flexible catheter body having a proximal end, a distal end and at least one lumen;
   an ultrasound transmission member extending longitudinally through the lumen of the catheter body and having a proximal end and a distal end;
   a distal head coupled with the distal end of the ultrasound transmission member and disposed adjacent the distal end of the catheter body;
   a sonic connector coupled with the proximal end of the ultrasound transmission member for coupling the ultrasound transmission member with an ultrasound transducer device; and
   a proximal housing coupled with the proximal end of the catheter body and housing the sonic connector and a proximal portion of the ultrasound transmission member,
   a heat absorption member disposed around the ultrasound transmission member, the heat absorption member comprising a metalized elastomer;
   a first O-ring member disposed around the ultrasound transmission member, and disposed proximal to the heat absorption member; and
   a second O-ring member disposed around the ultrasound transmission member, and disposed distal to the heat absorption member.

2. An ultrasound catheter as in claim 1, wherein one or more portions of the proximal housing comprise a heat conductive material.

3. An ultrasound catheter as in claim 2, wherein the heat conductive material is selected from the group consisting of metal, polymer, glass, rubber and combinations thereof.

4. An ultrasound catheter as in claim 1 or 2, wherein the proximal housing comprises multiple surface features to increase a surface area of the proximal housing.

5. An ultrasound catheter as in claim 4, wherein the surface features are selected from the group consisting of grooves, notches, waves and dips.

6. An ultrasound catheter as in claim 1 or 2, further comprising at least one conductive material disposed within the proximal housing, at least partially encircling the ultrasound transmission member, to conduct heat away from the ultrasound transmission member.

7. An ultrasound catheter as in claim 6, wherein the conductive material is disposed adjacent one or more vibration absorption members surrounding the ultrasound transmission member.

8. An ultrasound catheter as in claim 7, wherein the at least one conductive material comprises multiple separate conductive members disposed between multiple vibration absorption members and at least partially encircling the ultrasound transmission member.

9. An ultrasound catheter as in claim 6, wherein the conductive material is arranged over one or more vibration absorption members surrounding the ultrasound transmission member.

10. An ultrasound catheter as in claim 1, wherein at least a portion of the proximal housing comprises a material adapted to change color when the temperature of the housing changes.

11. An ultrasound catheter as in claim 10, wherein the material comprises a thermochromic pigment.

12. An ultrasound catheter as in claim 11, wherein the thermochromic pigment changes from a first color to a second color when the temperature of the housing reaches approximately 45° Celsius and changes from the second color to the first color when the temperature of the housing drops below approximately 45° Celsius.

13. An ultrasound catheter for disrupting occlusions in blood vessels, the ultrasound catheter comprising:
    an elongate flexible catheter body having a proximal end, a distal end and at least one lumen;
    an ultrasound transmission member extending longitudinally through the lumen of the catheter body and having a proximal end and a distal end;
    a distal head coupled with the distal end of the ultrasound transmission member and disposed adjacent the distal end of the catheter body;
    a sonic connector coupled with the proximal end of the ultrasound transmission member for coupling the ultrasound transmission member with an ultrasound transducer device; and
    a proximal housing coupled with the proximal end of the catheter body and housing the sonic connector and a proximal portion of the ultrasound transmission wire, and member; and
    a plurality of O-ring members disposed around and contacting a portion of the ultrasound transmission member wherein the proximal housing comprises a fluid inlet for allowing passage of one or more heat dissipating fluids into an inner cavity of the proximal housing, and wherein the inlet is disposed along the proximal housing such that the heat dissipating fluid(s) passing through the inlet flows within the inner cavity, and across the plurality of 0-ring members in a distal direction before contacting the ultrasound transmission member.

14. An ultrasound catheter as in claim 13, wherein the inner cavity of the housing is in fluid communication with the lumen of the catheter body, such that fluid introduced into the inner cavity passes through and out a distal end of the catheter body lumen.

15. An ultrasound catheter as in claim 13, wherein the inlet is disposed along the housing such that the heat dissipating fluid(s) passing through the inlet contact the sonic connector and the portion of the ultrasound transmission member.

16. An ultrasound catheter as in claim 13, further comprising a refrigeration deyice coupled with the catheter for refrigerating a fluid to be introduced through the fluid inlet.

17. An ultrasound catheter as in claim 13, further comprising a guidewire tube extending through at least a portion of the catheter body for allowing passage of a guidewire.

18. An ultrasound catheter as in claim 17, wherein a sidewall of the guidewire tube includes a plurality of apertures for allowing fluid introduced into the lumen of the catheter body to pass into and through the guidewire tube.

19. An ultrasound catheter for disrupting occlusions in blood vessels, the ultrasound catheter comprising:
    an elongate flexible catheter body having a proximal end, a distal end and at least one lumen;
    an ultrasound transmission member extending longitudinally through the lumen of the catheter body and having a proximal end and a distal end;
    a distal head coupled with the distal end of the ultrasound transmission member and disposed adjacent the distal end of the catheter body;
    a sonic connector coupled with the proximal end of the ultrasound transmission member for coupling the ultrasound transmission member with an ultrasound transducer device;
    a vibration absorption member disposed around a portion of the ultrasound transmission member; and
    a proximal housing coupled with the proximal end of the catheter body and housing the sonic connector and a proximal portion of the ultrasound transmission wire;
    wherein the proximal housing comprises a fluid inlet port for allowing passage of a heat dissipating fluid into an inner cavity of the proximal housing, and wherein the fluid inlet port is disposed along the proximal housing such that the heat dissipating fluid passing through the fluid inlet flows across a portion of the ultrasound transmission member proximal to the vibration absorption member, then flows across the vibration absorption member in a distal direction before contacting a portion of the ultrasound transmission member distal to the vibration absorption member.

20. An ultrasound catheter as in claim 19, wherein the proximal housing compnses one or more portions constructed of a heat conductive material.

21. An ultrasound catheter as in claim 20, wherein the heat conductive material is selected from the group consisting of metal, polymer, glass, rubber and combinations thereof.

22. An ultrasound catheter as in claim 20, wherein the proximal housing further comprises multiple surface features on the proximal housing to increase a surface area of the proximal housing.

23. An ultrasound catheter as in claim 22, wherein the surface features are selected from the group consisting of grooves, notches, waves and dips.

24. An ultrasound catheter as in claim 19, further comprising at least one conductive material disposed within the proximal housing, at least partially encircling the ultrasound transmission member, to conduct heat away from the ultrasound transmission member.

25. An ultrasound catheter as in claim 24, wherein the conductive material is disposed adjacent the vibration absorption members.

26. An ultrasound catheter as in claim 25, further comprising multiple vibration absorption members, wherein the conductive material comprises multiple separate conductive members disposed between the multiple vibration absorption members and at least partially encircling the ultrasound transmission member.

27. An ultrasound catheter as in claim 24, wherein the conductive material is arranged over one or more vibration absorption members surrounding the ultrasound transmission member.

28. An ultrasound catheter as in claim 19, wherein at least a portion of the proximal housing comprises a material adapted to change color when the temperature of the housing changes.

29. An ultrasound catheter as in claim 28, wherein the material comprises a thermochromic pigment.

30. An ultrasound catheter as in claim 29, wherein the thermochromic pigment changes from a first color to a second color when the temperature of the housing reaches approximately 45° Celsius and changes from the second color to the first color when the temperature of the housing drops below approximately 45° Celsius.

31. An ultrasound catheter for disrupting occlusions in blood vessels, the ultrasound catheter comprising:
   an elongate flexible catheter body having a proximal end, a distal end and at least one lumen;
   an ultrasound transmission member extending longitudinally through the lumen of the catheter body and having a proximal end and a distal end;
   a distal head coupled with the distal end of the ultrasound transmission member and disposed adjacent the distal end of the catheter body;
   a sonic connector coupled with the proximal end of the ultrasound transmission member for coupling the ultrasound transmission member with an ultrasound transducer device;
   an O-ring member disposed around a portion of the ultrasound transmission member; and
   a proximal housing coupled with the proximal end of the catheter body and housing the sonic connector and a proximal portion of the ultrasound transmission-wi*e member;
   wherein the proximal housing comprises a fluid inlet port for allowing passage of a heat dissipating fluid into an inner cavity of the proximal housing, and wherein the fluid inlet port is disposed along the proximal housing such that the heat dissipating fluid passing through the fluid inlet flows across a portion of the ultrasound transmission member proximal to the O-ring member, then flows across the O-ring member in a distal direction before contacting a portion of the ultrasound transmission member distal to the vibration absorption member.

32. An ultrasound catheter as in claim 31, wherein the inner cavity of the housing is in fluid communication with the lumen of the catheter body, such that fluid introduced into the inner cavity passes through and out a distal end of the catheter body lumen.

33. An ultrasound catheter as in claim 31, wherein the inlet is disposed along the housing such that the heat dissipating fluid(s) passing through the inlet contact a proximal portion of the ultrasound transmission member.

34. An ultrasound catheter as in claim 31, wherein the inlet is disposed along the housing such that the heat dissipating fluid passing through the inlet contact the sonic connector and the portion of the ultrasound transmission member.

35. An ultrasound catheter as in claim 31, further comprising a refrigeration device coupled with the catheter for refrigerating a fluid to be introduced through the fluid inlet.

36. An ultrasound catheter as in claim 31, further comprising a guidewire tube extending through at least a portion of the catheter body for allowing passage of a guidewire.

37. An ultrasound catheter as in claim 36, wherein a sidewall of the guidewire tube includes a plurality of apertures for allowing fluid introduced into the lumen of the catheter body to pass into and through the guidewire tube.

\* \* \* \* \*